(12) United States Patent
Jones et al.

(10) Patent No.: US 8,114,978 B2
(45) Date of Patent: Feb. 14, 2012

(54) METHODS FOR GENOTYPING SELECTED POLYMORPHISM

(75) Inventors: Keith W. Jones, Sunnyvale, CA (US); Michael H. Shapero, Redwood City, CA (US); Stephen P. A. Fodor, Palo Alto, CA (US)

(73) Assignee: Affymetrix, Inc., Santa Clara, CA (US)

( * ) Notice: Subject to any disclaimer, the term of this patent is extended or adjusted under 35 U.S.C. 154(b) by 394 days.

(21) Appl. No.: 12/326,596

(22) Filed: Dec. 2, 2008

(65) Prior Publication Data

US 2011/0009294 A1 Jan. 13, 2011

(51) Int. Cl.
*C07H 21/04* (2006.01)
*C12Q 1/68* (2006.01)
*C12P 19/34* (2006.01)

(52) U.S. Cl. .................. 536/24.3; 536/24.2; 536/24.33; 435/6.12; 435/91.2

(58) Field of Classification Search .................. None
See application file for complete search history.

(56) References Cited

U.S. PATENT DOCUMENTS

| | | | |
|---|---|---|---|
| 5,002,867 A | 3/1991 | Macevicz | |
| 5,143,854 A | 9/1992 | Pirrung et al. | |
| 5,202,231 A | 4/1993 | Drmanac et al. | |
| 5,387,505 A | 2/1995 | Wu | |
| 5,492,806 A | 2/1996 | Drmanac et al. | |
| 5,498,535 A | 3/1996 | Fomenkov et al. | |
| 5,501,964 A | 3/1996 | Wigler et al. | |
| 5,508,169 A | 4/1996 | Deugau et al. | |
| 5,580,730 A | 12/1996 | Okamoto | |
| 5,582,989 A | 12/1996 | Caskey et al. | |
| 5,624,825 A | 4/1997 | Walker et al. | |
| 5,667,972 A | 9/1997 | Drmanac et al. | |
| 5,695,940 A | 12/1997 | Drmanac et al. | |
| 5,700,637 A | 12/1997 | Southern | |
| 5,700,642 A | 12/1997 | Monforte et al. | |
| 5,710,000 A | 1/1998 | Sapolsky et al. | |
| 5,776,753 A | 7/1998 | Hillman et al. | |
| 5,854,033 A | 12/1998 | Lizardi | |

(Continued)

FOREIGN PATENT DOCUMENTS

EP 0534858 3/1993

(Continued)

OTHER PUBLICATIONS

Ahern, H. Biochemical, reagents kits offer scientists good return on investment. The Scientist, vol. 9, No. 15 [online] Jul. 24, 1995 [retrieved on Feb. 14, 2011] retrieved from: http://www.the-scientist.com/article/display/16618/ (5 pages).*

(Continued)

*Primary Examiner* — Samuel Woolwine
(74) *Attorney, Agent, or Firm* — Sandra E. Wells

(57) ABSTRACT

Methods for genotyping polymorphisms using a locus specific primer that is complementary to a region near a selected polymorphism are described. Methods for synthesizing pools of locus specific primers that incorporate some degenerate positions are also disclosed. A plurality of different sequence capture probes are synthesized simultaneously using degenerate oligonucleotide synthesis. The sequence of the locus specific regions of the capture probes are related in that they have some bases that are identical in each sequence in the plurality of sequences and positions that vary from one locus specific region to another. The sequences are selected based on proximity to a polymorphism of interest and because they conform to a similar sequence pattern.

12 Claims, 6 Drawing Sheets

U.S. PATENT DOCUMENTS

| | | | |
|---|---|---|---|
| 5,858,656 | A | 1/1999 | Degau et al. |
| 5,858,671 | A | 1/1999 | Jones |
| 5,972,693 | A | 10/1999 | Rothberg et al. |
| 5,994,068 | A | 11/1999 | Guilfoyle et al. |
| 6,045,994 | A | 4/2000 | Zabeau et al. |
| 6,057,096 | A | 5/2000 | Rothschild et al. |
| 6,100,030 | A | 8/2000 | McCasky Feazel et al. |
| 6,103,463 | A | 8/2000 | Chetverin et al. |
| 6,197,510 | B1 | 3/2001 | Vinayagamoorthy |
| 6,232,066 | B1 | 5/2001 | Felder et al. |
| 6,248,877 | B1 | 6/2001 | Bonner et al. |
| 6,258,539 | B1 | 7/2001 | Hunkapiller et al. |
| 6,280,935 | B1 | 8/2001 | Macevicz |
| 6,280,950 | B1 | 8/2001 | Lipshutz et al. |
| 6,322,971 | B1 | 11/2001 | Chetverin et al. |
| 6,352,828 | B1 | 3/2002 | Brenner |
| 6,355,431 | B1 | 3/2002 | Chee et al. |
| 6,361,947 | B1 | 3/2002 | Dong et al. |
| 6,509,160 | B1 | 1/2003 | Sapolsky et al. |
| 6,521,428 | B1 | 2/2003 | Senapathy |
| 6,703,228 | B1 | 3/2004 | Landers et al. |
| 6,720,179 | B1 | 4/2004 | Macevicz |
| 6,773,886 | B2 | 8/2004 | Kaufman et al. |
| 6,777,187 | B2 | 8/2004 | Makarov et al. |
| 6,812,005 | B2 | 11/2004 | Fan et al. |
| 7,108,976 | B2 | 9/2006 | Jones et al. |
| 7,297,778 | B2 | 11/2007 | Matsuzaki et al. |
| 2001/0053519 | A1* | 12/2001 | Fodor et al. ..................... 435/6 |
| 2003/0036069 | A1 | 2/2003 | Su |
| 2004/0067493 | A1 | 4/2004 | Matsuzaki et al. |
| 2004/0110153 | A1 | 6/2004 | Dong et al. |
| 2005/0100911 | A1 | 5/2005 | Patil et al. |
| 2005/0148004 | A1 | 7/2005 | Wober et al. |
| 2006/0063158 | A1 | 3/2006 | Dong et al. |
| 2006/0073501 | A1 | 4/2006 | Van Den Boom et al. |
| 2006/0246457 | A1 | 11/2006 | Dirks et al. |
| 2007/0065816 | A1 | 3/2007 | Dong et al. |

FOREIGN PATENT DOCUMENTS

| | | |
|---|---|---|
| EP | 1350853 A1 | 10/2003 |
| WO | WO 96/41893 | 12/1996 |
| WO | WO 01/88174 A1 | 11/2001 |

OTHER PUBLICATIONS

Broude et al., High Level Mulitplex DNA Amplification; *Antisense & Nucleic Acid Drug Development*, 2001, 11: 327-332.

Broude et al., Mulitplex Allele-Specific Target Amplifcation Based on PCR Suppression, *PNA*, Jan. 2, 2001, 98:1, 206-211.

Craig et al., Removal of Repetitive Sequences from FISH probes using PCR-assisted affinity chomatography; Human Genetics, vol. 100, No. 3-4, 1997, pp. 472-476.

Durm et al., Fast-painting of Human Methaphase Spreads Using a Chromosome-Specific, Repeat-Depleted DNA Library Probe; Biotechniques, Eaton Publishing; Vo. 24; No. 5; May 1988; pp. 820-825.

Siebert et al., An Improved PCR Method for Walking an Uncloned Genomic DNA, *Nucleic Acids Research*, 1995, 23:6, 1087-1088.

* cited by examiner

SEQUENCE LISTING

```
<160> NUMBER OF SEQ ID NOS: 5

<210> SEQ ID NO 1
<211> LENGTH: 14
<212> TYPE: DNA
<213> ORGANISM: Artificial
<220> FEATURE:
<223> OTHER INFORMATION: Synthetic Sequence.
<220> FEATURE:
<221> NAME/KEY: misc_feature
<222> LOCATION: (3)..(4)
<223> OTHER INFORMATION: n is a, c, g, or t
<220> FEATURE:
<221> NAME/KEY: misc_feature
<222> LOCATION: (7)..(10)
<223> OTHER INFORMATION: n is a, c, g, or t

<400> SEQUENCE: 1
acnngtnnnn aatt                                                      14

<210> SEQ ID NO 2
```

```
-continued
<211> LENGTH: 14
<212> TYPE: DNA
<213> ORGANISM: artificial
<220> FEATURE:
<223> OTHER INFORMATION: Synthetic Sequence.

<400> SEQUENCE: 2
aatttaccac gtgt                                                            14

<210> SEQ ID NO 3
<211> LENGTH: 14
<212> TYPE: DNA
<213> ORGANISM: Artificial
<220> FEATURE:
<223> OTHER INFORMATION: Synthetic Sequence.

<400> SEQUENCE: 3
aattgcaaac ccgt                                                            14

<210> SEQ ID NO 4
<211> LENGTH: 12
<212> TYPE: DNA
<213> ORGANISM: Artificial
<220> FEATURE:
<223> OTHER INFORMATION: Synthetic Sequence.
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (5)..(7)
<223> OTHER INFORMATION: n is a, c, g, or t

<400> SEQUENCE: 4
nngannnatt aa                                                              12

<210> SEQ ID NO 5
<211> LENGTH: 37
<212> TYPE: DNA
<213> ORGANISM: Artificial
<220> FEATURE:
<223> OTHER INFORMATION: Synthetic Sequence.
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (30)..(33)
<223> OTHER INFORMATION: n is a, c, g, or t

<400> SEQUENCE: 5
taatacgact cactataggg agaacnngtn nnnaatt                                   37
```

METHODS FOR GENOTYPING SELECTED POLYMORPHISM

RELATED APPLICATIONS

The present application claims priority to U.S. Provisional application No. 60/493,085, filed Aug. 5, 2003, the entire disclosure of which is incorporated herein by reference in its entirety.

FIELD OF THE INVENTION

The invention relates to enrichment and amplification of a collection of target sequences from a nucleic acid sample and methods of analyzing amplified product. In some embodiments target sequences are amplified by extension of a locus-specific primer followed by amplification of the extended locus-specific primer with a generic pair of primers. In some embodiments the locus-specific primers are attached to a solid support and extension takes place on the solid support. In some embodiments the invention relates to the preparation of target for array based analysis of genotype. The present invention relates to the fields of molecular biology and genetics.

BACKGROUND OF THE INVENTION

The past years have seen a dynamic change in the ability of science to comprehend vast amounts of data. Pioneering technologies such as nucleic acid arrays allow scientists to delve into the world of genetics in far greater detail than ever before. Exploration of genomic DNA has long been a dream of the scientific community. Held within the complex structures of genomic DNA lies the potential to identify, diagnose, or treat diseases like cancer, Alzheimer disease or alcoholism. Exploitation of genomic information from plants and animals may also provide answers to the world's food distribution problems.

Recent efforts in the scientific community, such as the publication of the draft sequence of the human genome in February 2001, have changed the dream of genome exploration into a reality. Genome-wide assays, however, must contend with the complexity of genomes; the human genome for example is estimated to have a complexity of $3 \times 10^9$ base pairs. Novel methods of sample preparation and sample analysis that reduce complexity may provide for the fast and cost effective exploration of complex samples of nucleic acids, particularly genomic DNA.

SUMMARY OF THE INVENTION

A method of genotyping a plurality of polymorphisms present in target sequences is disclosed. A pool of potential target polymorphisms is selected and the sequences near the polymorphism are analyzed to identify a sequence for targeting a locus specific primer. The sequence comprises a common sequence and a consensus sequence. The common sequence is a stretch of at least 4 bases that are identical in each target sequence. The consensus sequence comprises a region that has some bases that are identical in all target sequences and some bases that are variable between target sequences. The polymorphisms to be analyzed may be selected based on the presence of the common and consensus sequences. Preferably the common and consensus sequences are immediately adjacent to one another and more preferably the common sequence is between the consensus sequence and the polymorphic position so that a primer containing the consensus sequence 5' of the common sequence can be extended in the direction of the polymorphic position. The consensus sequence may be first identified by identifying a common sequence that is present in many of the targets, such as a restriction enzyme recognition site and then analyzing the sequence that is immediately adjacent to the common sequence in a plurality of potential target sequences. The sequences surrounding the common sequence are then analyzed to identify a target sequences that have similar sequence immediately adjacent to the common sequence. In this way a plurality of targets, containing polymorphisms, are identified that can be hybridized to a pool of primers or capture probes that are synthesized in the same degenerate synthesis reaction or in a limited number of synthesis reactions that include pooled and separate monomer addition steps.

The pool of capture probes is hybridized to genomic DNA, which may be adaptor ligated fragment, and extended through the polymorphism. The extended capture probes may be amplified, by PCR for example. The amplification product may be hybridized to an array of probes designed to discriminate between different alleles of a polymorphic allele so that the base or bases present at the polymorphic positions may be determined.

An array comprising allele specific probes for the polymorphic positions to be genotyped is also disclosed. The probes of the array are selected based on the target sequences that are selected. Hybridization to the array is analyzed to determine the bases present at the polymorphic positions.

Kits for performing the disclosed methods are also disclosed. The kits may comprise pools of capture probes designed for amplification of a plurality of target sequences. The target sequences are selected so that they each contain a polymorphic position of interest, they each share a common sequence and a consensus sequence that is immediately adjacent to the common sequence, and the common sequence is within 1000 base pairs of the polymorphic position. The common sequence is the same in a plurality of targets and the consensus sequence has positions that are identical in each target sequence and positions that are variable between target sequences. The capture probes are complementary to the common and consensus sequences and also comprises a universal priming sequence that is 5' of the region that is complementary to the target. The capture probes may be pooled into containers that contain 2 or more different sequence capture probes. Preferably 100 or more different sequence capture probes are pooled into a single container. The capture probes may be synthesized by combinatorial methods and may include steps where a mixture of bases is added. The kit may further comprise adaptors, universal primers, dNTPs, ligase, buffer, and polymerase.

The kits may be used to amplify a collection of target sequences. Amplification may be by fragmentation of the sample, ligation of an adaptor to the fragments, hybridization of capture probes to the adaptor-ligated fragments, extension of the capture probe, and amplification of the extended capture probes using a pair of universal primers.

BRIEF DESCRIPTION OF THE FIGURES

FIG. 5 shows schematics of combinatorial synthesis of degenerate primers on an array.

FIG. 6 shows a comparison of synthesis methods.

Figure 1:
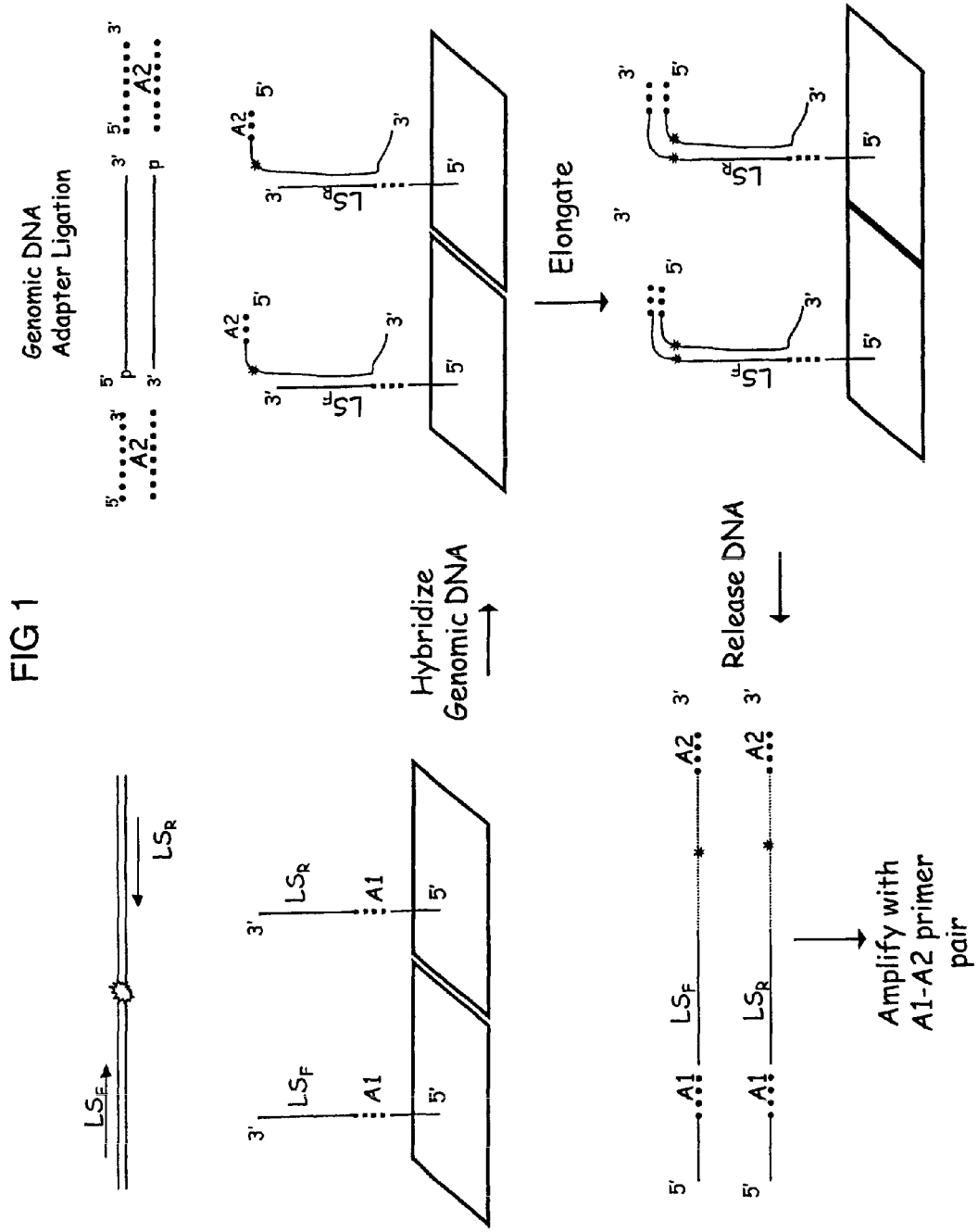
FIG. 1 shows a method of amplifying specific target sequences using a capture probe that is locus specific and genomic DNA that has been ligated to an adaptor. The capture probes are attached to a solid support and extended to incorporate the sequence of interest and the adaptor sequence. The extended capture probes are released from the solid support and amplified with a single primer pair.

DETAILED DESCRIPTION OF THE PREFERRED EMBODIMENTS (A.) General

The present invention has many preferred embodiments and relies on many patents, applications and other references for details known to those of the art. Therefore, when a patent, application, or other reference is cited or repeated below, it should be understood that it is incorporated by reference in its entirety for all purposes as well as for the proposition that is recited.

As used in this application, the singular form "a," "an," and "the" include plural references unless the context clearly dictates otherwise. For example, the term "an agent" includes a plurality of agents, including mixtures thereof.

An individual is not limited to a human being but may also be other organisms including but not limited to mammals, plants, bacteria, or cells derived from any of the above.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series (Vols. I-IV)*, *Using Antibodies: A Laboratory Manual*, *Cells: A Laboratory Manual*, *PCR Primer: A Laboratory Manual*, and *Molecular Cloning: A Laboratory Manual* (all from Cold Spring Harbor Laboratory Press), Stryer, L. (1995) *Biochemistry* (4th Ed.) Freeman, New York, Gait, "Oligonucleotide Synthesis: A Practical Approach" 1984, IRL Press, London, Nelson and Cox (2000), *Lehninger, Principles of Biochemistry* $3^{rd}$ Ed., W.H. Freeman Pub., New York, N.Y. and Berg et al. (2002) *Biochemistry*, $5^{th}$ Ed., W.H. Freeman Pub., New York, N.Y., all of which are herein incorporated in their entirety by reference for all purposes.

The present invention can employ solid substrates, including arrays in some preferred embodiments. Methods and techniques applicable to polymer (including protein) array synthesis have been described in U.S. Ser. No. 09/536,841, WO 00/58516, U.S. Pat. Nos. 5,143,854, 5,242,974, 5,252,743, 5,324,633, 5,384,261, 5,405,783, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, 6,136,269, 6,269,846 and 6,428,752, in PCT Applications Nos. PCT/US99/00730 (International Publication Number WO 99/36760) and PCT/US01/04285, which are all incorporated herein by reference in their entirety for all purposes.

Patents that describe synthesis techniques in specific embodiments include U.S. Pat. Nos. 5,412,087, 6,147,205, 6,262,216, 6,310,189, 5,889,165, and 5,959,098. Nucleic acid arrays are described in many of the above patents, but the same techniques are applied to polypeptide arrays.

Nucleic acid arrays that are useful in the present invention include those that are commercially available from Affymetrix (Santa Clara, Calif.) under the brand name GeneChip®. Example arrays are shown on the website at affymetrix.com.

The present invention also contemplates many uses for polymers attached to solid substrates. These uses include gene expression monitoring, profiling, library screening, genotyping and diagnostics. Gene expression monitoring and profiling methods can be shown in U.S. Pat. Nos. 5,800,992, 6,013,449, 6,020,135, 6,033,860, 6,040,138, 6,177,248 and 6,309,822. Genotyping and uses therefore are shown in U.S. Ser. No. 60/319,253, Ser. No. 10/013,598, and U.S. Pat. Nos. 5,856,092, 6,300,063, 5,858,659, 6,284,460, 6,361,947, 6,368,799 and 6,333,179. Other uses are embodied in U.S. Pat. Nos. 5,871,928, 5,902,723, 6,045,996, 5,541,061, and 6,197,506.

The present invention also contemplates sample preparation methods in certain preferred embodiments. Prior to or concurrent with genotyping, the genomic sample may be amplified by a variety of mechanisms, some of which may employ PCR. See, e.g., *PCR Technology: Principles and Applications for DNA Amplification* (Ed. H.A. Erlich, Freeman Press, NY, N.Y., 1992); *PCR Protocols: A Guide to Methods and Applications* (Eds. Innis, et al., Academic Press, San Diego, Calif., 1990); Mattila et al., *Nucleic Acids Res.* 19, 4967 (1991); Eckert et al., *PCR Methods and Applications* 1, 17 (1991); *PCR* (Eds. McPherson et al., IRL Press, Oxford); and U.S. Pat. Nos. 4,683,202, 4,683,195, 4,800,159 4,965,188, and 5,333,675, and each of which is incorporated herein by reference in their entireties for all purposes. The sample may be amplified on the array. See, for example, U.S. Pat. No, 6,300,070 and U.S. patent application Ser. No. 09/513,300, which are incorporated herein by reference.

Other suitable amplification methods include the ligase chain reaction (LCR) (e.g., Wu and Wallace, *Genomics* 4, 560 (1989), Landegren et al., *Science* 241, 1077 (1988) and Barringer et al. *Gene* 89:117 (1990)), transcription amplification (Kwoh et al., *Proc. Natl. Acad. Sci. USA* 86, 1173 (1989) and WO88/10315), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909, 5,861,245), degenerate oligonucleotide primed PCR (DOP-PCR), (Telenius H., et al. *Genomics* 13:718-25 (1992)), self-sustained sequence replication (Guatelli et al., *Proc. Nat. Acad. Sci. USA,* 87, 1874 (1990) and WO90/06995) and nucleic acid based sequence amplification (NABSA). (See, U.S. Pat. Nos. 5,409,818, 5,554,517, and 6,063,603, each of which is incorporated herein by reference). The latter two amplification methods involve isothermal reactions based on isothermal transcription, which produce both single stranded RNA (ssRNA) and double stranded DNA (dsDNA) as the amplification products in a ratio of about 30 or 100 to 1, respectively. Other amplification methods that may be used are described in, U.S. Pat. Nos. 5,242,794, 5,494,810, 4,988,617 and in U.S. Ser. No. 09/854,317, each of which is incorporated herein by reference.

Additional methods of sample preparation and techniques for reducing the complexity of a nucleic sample are described in Dong et al., *Genome Research* 11, 1418 (2001), in U.S. Pat. Nos. 6,361,947, 6,391,592 and U.S. patent application Ser. Nos. 09/916,135, 09/920,491, 09/910,292, and 10/013,598.

Methods for conducting polynucleotide hybridization assays have been well developed in the art. Hybridization assay procedures and conditions will vary depending on the application and are selected in accordance with the general binding methods known including those referred to in: Maniatis et al. *Molecular Cloning: A Laboratory Manual* (3$^{rd}$ Ed. Cold Spring Harbor, N.Y., 2002); Berger and Kimmel *Methods in Enzymology*, Vol. 152, *Guide to Molecular Cloning Techniques* (Academic Press, Inc., San Diego, Calif., 1987); Young and Davism, *P.N.A.S,* 80: 1194 (1983). Methods and apparatus for carrying out repeated and controlled hybridization reactions have been described in U.S. Pat. Nos. 5,871,928, 5,874,219, 6,045,996 and 6,386,749, 6,391,623 each of which are incorporated herein by reference The present invention also contemplates signal detection of hybridization between ligands in certain preferred embodiments. See U.S. Pat. Nos. 5,143,854, 5,578,832; 5,631,734; 5,834,758; 5,936,324; 5,981,956; 6,025,601; 6,141,096; 6,185,030; 6,201,639; 6,218,803; and 6,225,625, in U.S. Patent application 60/364,731 and in PCT Application PCT/US99/06097 (published as WO99/47964), each of which also is hereby incorporated by reference in its entirety for all purposes.

Methods and apparatus for signal detection and processing of intensity data are disclosed in, for example, U.S. Pat. Nos. 5,143,854, 5,547,839, 5,578,832, 5,631,734, 5,800,992, 5,834,758; 5,856,092, 5,902,723, 5,936,324, 5,981,956, 6,025,601, 6,090,555, 6,141,096, 6,185,030, 6,201,639; 6,218,803; and 6,225,625, in U.S. Patent application 60/364,731 and in PCT Application PCT/US99/06097 (published as WO99/47964), each of which also is hereby incorporated by reference in its entirety for all purposes.

The practice of the present invention may also employ conventional biology methods, software and systems. Computer software products of the invention typically include computer readable medium having computer-executable instructions for performing the logic steps of the method of the invention. Suitable computer readable medium include floppy disk, CD-ROM/DVD/DVD-ROM, hard-disk drive, flash memory, ROM/RAM, magnetic tapes and etc. The computer executable instructions may be written in a suitable computer language or combination of several languages. Basic computational biology methods are described in, e.g. Setubal and Meidanis et al., *Introduction to Computational Biology Methods* (PWS Publishing Company, Boston, 1997); Salzberg, Searles, Kasif, (Ed.), *Computational Methods in Molecular Biology*, (Elsevier, Amsterdam, 1998); Rashidi and Buehler, *Bioinformatics Basics: Application in Biological Science and Medicine* (CRC Press, London, 2000) and Ouelette and Bzevanis *Bioinformatics: A Practical Guide for Analysis of Gene and Proteins* (Wiley & Sons, Inc., 2$^{nd}$ ed., 2001).

The present invention may also make use of various computer program products and software for a variety of purposes, such as probe design, management of data, analysis, and instrument operation. See, U.S. Pat. Nos. 5,593,839, 5,795,716, 5,733,729, 5,974,164, 6,066,454, 6,090,555, 6,185,561, 6,188,783, 6,223,127, 6,229,911 and 6,308,170.

Additionally, the present invention may have preferred embodiments that include methods for providing genetic information over networks such as the Internet as shown in U.S. patent application Ser. Nos. 10/063,559, 60/349,546, 60/376,003, 60/394,574, 60/403,381.

(B.) Definitions

The term "admixture" refers to the phenomenon of gene flow between populations resulting from migration. Admixture can create linkage disequilibrium (LD).

The term "allele" as used herein is any one of a number of alternative forms a given locus (position) on a chromosome. An allele may be used to indicate one form of a polymorphism, for example, a biallelic SNP may have possible alleles A and B. An allele may also be used to indicate a particular combination of alleles of two or more SNPs in a given gene or chromosomal segment. The frequency of an allele in a population is the number of times that specific allele appears divided by the total number of alleles of that locus.

The term "genome" as used herein is all the genetic material in the chromosomes of an organism. DNA derived from the genetic material in the chromosomes of a particular organism is genomic DNA. A genomic library is a collection of clones made from a set of randomly generated overlapping DNA fragments representing the entire genome of an organism.

The term "genotype" as used herein refers to the genetic information an individual carries at one or more positions in the genome. A genotype may refer to the information present at a single polymorphism, for example, a single SNP. For example, if a SNP is biallelic and can be either an A or a C then if an individual is homozygous for A at that position the genotype of the SNP is homozygous A or AA. Genotype may also refer to the information present at a plurality of polymorphic positions.

The term "Hardy-Weinberg equilibrium" (HWE) as used herein refers to the principle that an allele that when homozygous leads to a disorder that prevents the individual from reproducing does not disappear from the population but remains present in a population in the undetectable heterozygous state at a constant allele frequency.

The term "linkage analysis" as used herein refers to a method of genetic analysis in which data are collected from affected families, and regions of the genome are identified that co-segregated with the disease in many independent families or over many generations of an extended pedigree. A disease locus may be identified because it lies in a region of the genome that is shared by all affected members of a pedigree.

The term "linkage disequilibrium" or sometimes referred to as "allelic association" as used herein refers to the preferential association of a particular allele or genetic marker with a specific allele, or genetic marker at a nearby chromosomal location more frequently than expected by chance for any particular allele frequency in the population. For example, if locus X has alleles A and B, which occur equally frequently, and linked locus Y has alleles C and D, which occur equally frequently, one would expect the combination AC to occur with a frequency of 0.25. If AC occurs more frequently, then alleles A and C are in linkage disequilibrium. Linkage disequilibrium may result from natural selection of certain combination of alleles or because an allele has been introduced into a population too recently to have reached equilibrium with linked alleles. The genetic interval around a disease locus may be narrowed by detecting disequilibrium between nearby markers and the disease locus. For additional information on linkage disequilibrium see Ardlie et al., *Nat. Rev. Gen.* 3:299-309, 2002.

The term "lod score" or "LOD" is the log of the odds ratio of the probability of the data occurring under the specific hypothesis relative to the null hypothesis. LOD=log [probability assuming linkage/probability assuming no linkage].

Nucleic acids according to the present invention may include any polymer or oligomer of pyrimidine and purine bases, preferably cytosine, thymine, and uracil, and adenine and guanine, respectively. (See Albert L. Lehninger, *Principles of Biochemistry*, at 793-800 (Worth Pub. 1982) which is herein incorporated in its entirety for all purposes). Indeed, the present invention contemplates any deoxyribonucleotide, ribonucleotide or peptide nucleic acid component, and any chemical variants thereof, such as methylated, hydroxymethylated or glucosylated forms of these bases, and the like. The polymers or oligomers may be heterogeneous or homogeneous in composition, and may be isolated from naturally occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

An "oligonucleotide" or "polynucleotide" is a nucleic acid ranging from at least 2, preferably at least 8, 15 or 20 nucleotides in length, but may be up to 50, 100, 1000, or 5000 nucleotides long or a compound that specifically hybridizes to a polynucleotide. Polynucleotides of the present invention include sequences of deoxyribonucleic acid (DNA) or ribonucleic acid (RNA) or mimetics thereof which may be isolated from natural sources, recombinantly produced or artificially synthesized. A further example of a polynucleotide of the present invention may be a peptide nucleic acid (PNA). (See U.S. Pat. No. 6,156,501 which is hereby incorporated by reference in its entirety.) The invention also encompasses situations in which there is a nontraditional base pairing such as Hoogsteen base pairing which has been identified in certain tRNA molecules and postulated to exist in a triple helix. "Polynucleotide" and "oligonucleotide" are used interchangeably in this application.

The term "fragment," "segment," or "DNA segment" refers to a portion of a larger DNA polynucleotide or DNA. A polynucleotide, for example, can be broken up, or fragmented into, a plurality of segments. Various methods of fragmenting nucleic acid are well known in the art. These methods may be, for example, either chemical or physical in nature. Chemical fragmentation may include partial degradation with a DNase; partial depurination with acid; the use of restriction enzymes; intron-encoded endonucleases; DNA-based cleavage methods, such as triplex and hybrid formation methods, that rely on the specific hybridization of a nucleic acid segment to localize a cleavage agent to a specific location in the nucleic acid molecule; or other enzymes or compounds which cleave DNA at known or unknown locations (see, for example, U.S. Ser. No. 09/358,664). Physical fragmentation methods may involve subjecting the DNA to a high shear rate. High shear rates may be produced, for example, by moving DNA through a chamber or channel with pits or spikes, or forcing the DNA sample through a restricted size flow passage, e.g., an aperture having a cross sectional dimension in the micron or submicron scale. Other physical methods include sonication and nebulization. Combinations of physical and chemical fragmentation methods may likewise be employed such as fragmentation by heat and ion-mediated hydrolysis. See for example, Sambrook et al., "Molecular Cloning: A Laboratory Manual," $3^{rd}$ Ed. Cold Spring Harbor Laboratory Press, Cold Spring Harbor, N.Y. (2001) ("Sambrook et al.) which is incorporated herein by reference for all purposes. These methods can be optimized to digest a nucleic acid into fragments of a selected size range. Useful size ranges may be from 100, 200, 400, 700 or 1000 to 500, 800, 1500, 2000, 4000 or 10,000 base pairs. However, larger size ranges such as 4000, 10,000 or 20,000 to 10,000, 20,000 or 500,000 base pairs may also be useful.

A number of methods disclosed herein require the use of restriction enzymes to fragment the nucleic acid sample. In general, a restriction enzyme recognizes a specific nucleotide sequence of four to eight nucleotides and cuts the DNA at a site within or a specific distance from the recognition sequence. For example, the restriction enzyme EcoRI recognizes the sequence GAATTC and will cut a DNA molecule between the G and the first A. The length of the recognition sequence is roughly proportional to the frequency of occurrence of the site in the genome. A simplistic theoretical estimate is that a six base pair recognition sequence will occur once in every 4096 ($4^6$) base pairs while a four base pair recognition sequence will occur once every 256 ($4^4$) base pairs. In silico digestions of sequences from the Human Genome Project show that the actual occurrences may be more or less frequent, depending on the sequence of the restriction site. Because the restriction sites are rare, the appearance of shorter restriction fragments, for example those less than 1000 base pairs, is much less frequent than the appearance of longer fragments. Many different restriction enzymes are known and appropriate restriction enzymes can be selected for a desired result. (For a description of many restriction enzymes and their recognition sites and optimal buffer conditions see, New England BioLabs Catalog which is herein incorporated by reference in its entirety for all purposes).

Type-IIs endonucleases are a class of endonucleases that, like other endonucleases, recognize specific sequences of nucleotide base pairs within a double stranded polynucleotide sequence. Upon recognizing that sequence, the endonuclease will cleave the polynucleotide sequence, generally leaving an overhang of one strand of the sequence, or "sticky end." The Type-IIs endonucleases are unique because they generally do not require palindromic recognition sequences and they generally cleave outside of their recognition sites. The recognition sequence is often non-palindromic, and the cleavage occurs outside of the recognition site.

Type-IIs endonucleases are generally commercially available and are well known in the art. Specific Type-IIs endonucleases which are useful in the present invention include, e.g., BbvI, BceAI, BfuAI, EarI, AlwI, BbsI, BsaI, BsmAI, BsmBI, BspMI, HgaI, SapI, SfaNI, BsmFI, FokI, and PleI. Other Type-IIs endonucleases that may be useful in the present invention may be found, for example, in the New England Biolabs catalogue. In some embodiments Type-IIs enzymes that generate a recessed 3' end are particularly useful.

"Adaptor sequences" or "adaptors" are generally oligonucleotides of at least 5, 10, 15 or 20 bases and preferably no more than 50 or 60 bases in length; however, they may be even longer, up to 100 or 200 bases. Adaptor sequences may be synthesized using any methods known to those of skill in the art. For the purposes of this invention they may, as options, comprise primer binding sites, recognition sites for endonucleases, common sequences and promoters. The adaptor may be entirely or substantially double stranded. A double stranded adaptor may comprise two oligonucleotides that are at least partially complementary. The adaptor may be phosphorylated or unphosphorylated on one or both strands. Adaptors may be more efficiently ligated to fragments if they comprise a substantially double stranded region and a short single stranded region which is complementary to the single stranded region created by digestion with a restriction enzyme. For example, when DNA is digested with the restriction enzyme EcoRI the resulting double stranded fragments are flanked at either end by the single stranded overhang 5'-AATT-3', an adaptor that carries a single stranded overhang 5'-AATT-3' will hybridize to the fragment through complementarity between the overhanging regions. This "sticky end" hybridization of the adaptor to the fragment may facilitate ligation of the adaptor to the fragment but blunt ended ligation is also possible. Blunt ends can be converted to sticky ends using the exonuclease activity of the Klenow fragment. For example when DNA is digested with PvuII the blunt ends can be converted to a two base pair overhang by incubating the fragments with Klenow in the presence of dTTP and dCTP. Overhangs may also be converted to blunt ends by filling in an overhang or removing an overhang.

An adaptor may be ligated to one or both strands of the fragmented DNA. In some embodiments a double stranded adaptor is used but only one strand is ligated to the fragments. Ligation of one strand of an adaptor may be selectively blocked. Any known method to block ligation of one strand may be employed. For example, one strand of the adapter can be designed to introduce a gap of one or more nucleotides between the 5' end of that strand of the adaptor and the 3' end of the target nucleic acid. Adaptors can be designed specifically to be ligated to the termini produced by restriction enzymes and to introduce gaps or nicks. For example, if the target is an EcoRI digested fragment an adaptor with a 5' overhang of TTA could be ligated to the AATT overhang left by EcoRI to introduce a single nucleotide gap between the adaptor and the 3' end of the fragment. Phosphorylation and kinasing can also be used to selectively block ligation of the adaptor to the 3' end of the target molecule. Absence of a phosphate from the 5' end of an adaptor will block ligation of that 5' end to an available 3'OH. For additional adaptor methods for selectively blocking ligation see U.S. Pat. No. 6,197, 557 and U.S. Ser. No. 09/910,292 which are incorporated by reference herein in their entirety for all purposes.

Adaptors may also incorporate modified nucleotides that modify the properties of the adaptor sequence. For example, phosphorothioate groups may be incorporated in one of the adaptor strands. A phosphorothioate group is a modified phosphate group with one of the oxygen atoms replaced by a sulfur atom. In a phosphorothioated oligo (often called an "S-Oligo"), some or all of the internucleotide phosphate groups are replaced by phosphorothioate groups. The modified backbone of an S-Oligo is resistant to the action of most exonucleases and endonucleases. Phosphorothioates may be incorporated between all residues of an adaptor strand, or at specified locations within a sequence. A useful option is to sulfurize only the last few residues at each end of the oligo. This results in an oligo that is resistant to exonucleases, but has a natural DNA center.

Methods of ligation will be known to those of skill in the art and are described, for example in Sambrook et at. (2001) and the New England BioLabs catalog both of which are incorporated herein by reference for all purposes. Methods include using T4 DNA Ligase which catalyzes the formation of a phosphodiester bond between juxtaposed 5' phosphate and 3' hydroxyl termini in duplex DNA or RNA with blunt and sticky ends; Tag DNA Ligase which catalyzes the formation of a phosphodiester bond between juxtaposed 5' phosphate and 3' hydroxyl termini of two adjacent oligonucleotides which are hybridized to a complementary target DNA; E. coli DNA ligase which catalyzes the formation of a phosphodiester bond between juxtaposed 5'-phosphate and 3'-hydroxyl termini in duplex DNA containing cohesive ends; and T4 RNA ligase which catalyzes ligation of a 5' phosphoryl-terminated nucleic acid donor to a 3' hydroxyl-terminated nucleic acid acceptor through the formation of a 3'->5' phosphodiester bond, substrates include single-stranded RNA and DNA as well as dinucleoside pyrophosphates; or any other methods described in the art.

When a fragment has been digested on both ends with the same enzyme or two enzymes that leave the same overhang, the same adaptor may be ligated to both ends. Digestion with two or more enzymes can be used to selectively ligate separate adaptors to either end of a restriction fragment. For example, if a fragment is the result of digestion with EcoRI at one end and BamHI at the other end, the overhangs will be 5'-AATT-3' and 5'GATC-3', respectively. An adaptor with an overhang of AATT will be preferentially ligated to one end while an adaptor with an overhang of GATC will be preferentially ligated to the second end.

A genome is all the genetic material of an organism. In some instances, the term genome may refer to the chromosomal DNA. Genome may be multichromosomal such that the DNA is cellularly distributed among a plurality of individual chromosomes. For example, in human there are 22 pairs of chromosomes plus a gender associated XX or XY pair. DNA derived from the genetic material in the chromosomes of a particular organism is genomic DNA. The term genome may also refer to genetic materials from organisms that do not have chromosomal structure. In addition, the term genome may refer to mitochondria DNA. A genomic library is a collection of DNA fragments representing the whole or a portion of a genome. Frequently, a genomic library is a collection of clones made from a set of randomly generated, sometimes overlapping DNA fragments representing the entire genome or a portion of the genome of an organism.

The term "chromosome" refers to the heredity-bearing gene carrier of a living cell which is derived from chromatin and which comprises DNA and protein components (especially histones). The conventional internationally recognized individual human genome chromosome numbering system is employed herein. The size of an individual chromosome can vary from one type to another with a given multi-chromosomal genome and from one genome to another. In the case of the human genome, the entire DNA mass of a given chromosome is usually greater than about 100,000,000 bp. For example, the size of the entire human genome is about $3 \times 10^9$ bp. The largest chromosome, chromosome no. 1, contains about $2.4 \times 10^8$ bp while the smallest chromosome, chromosome no. 22, contains about $5.3 \times 10^7$ bp.

A chromosomal region is a portion of a chromosome. The actual physical size or extent of any individual chromosomal region can vary greatly. The term region is not necessarily definitive of a particular one or more genes because a region need not take into specific account the particular coding segments (exons) of an individual gene.

An allele refers to one specific form of a genetic sequence (such as a gene) within a cell, an individual or within a population, the specific form differing from other forms of the same gene in the sequence of at least one, and frequently more than one, variant sites within the sequence of the gene. The sequences at these variant sites that differ between different alleles are termed "variances", "polymorphisms", or "mutations". At each autosomal specific chromosomal location or "locus" an individual possesses two alleles, one inherited from one parent and one from the other parent, for example one from the mother and one from the father. An individual is "heterozygous" at a locus if it has two different alleles at that locus. An individual is "homozygous" at a locus if it has two identical alleles at that locus.

Capture probes are oligonucleotides that have a 5' common priming sequence and a 3' locus or target specific region or primer. The locus or target specific region is designed to hybridize near a region of nucleic acid that includes a region of interest, for example, near a polymorphism, so that the locus or target specific region of the capture probe can be used as a primer and be extended through the region of interest to make a copy of the region of interest. The common priming sequence in the capture probe may be used as a priming site in subsequent rounds of amplification using a common primer or a limited number of common primers. The same common priming sequence may be present in many or all or the capture probes in a collection of capture probes so that extended capture probes can be amplified with a common sequence primer, for example T7 promoter primer. Capture probes may also comprise other sequences, for example, to tag sequences that are unique for different species of capture probes, and endonuclease recognition sites. In some embodiments the capture probe is designed to hybridize upstream of a polymorphic position so that the capture probe can be extended through the polymorphic position, thus incorporating a copy of the polymorphism into the extended capture probe. In some embodiments the target sample is fragmented prior to extension of the capture probes and extension terminates at the end of the fragments. The fragments may or may not be ligated to adaptors before capture probe extension. If the fragments are ligated to an adaptor sequence, the extended capture probe will be extended through the adaptor and will terminate in the adaptor sequence.

A degenerate capture probe is a capture probe that has a degenerate locus or target specific region or primer. The locus specific region is the region of the capture probe that is complementary to the target upstream of the polymorphism. The locus specific region is the 3' region of the capture probe so that it can hybridize to the target upstream of the polymorphism and be extended through the polymorphic site, thus incorporating the polymorphic base into the extended capture probe. A degenerate capture probe is synthesized with some positions being variable and some positions being fixed. For example, the locus specific region of a degenerate capture probe may be, for example, 5'-ACNNGTNNNNAATT-3' (SEQ ID No. 1). Positions 1, 2, 5, 6, and 11-14 are fixed and positions 3, 4, and 7-10 are variable and can be A, G, C or T.

A degenerate priming site is a site that is complementary to one possible species of a degenerate primer. For example, if the degenerate primer sequence is 5'-ACNNGT-NNNNAATT-3' (SEQ ID NO. 1) then degenerate priming sites would include, for example, 5'-AATTtaccACgtGT-3' (SEQ ID NO. 2) and 5'-AATTgcaaACccGT-3' (SEQ ID NO. 3). In these examples the lower case letters represent positions that may vary from probe to probe and the upper case letters are positions that are constant in all probes with that degenerate sequence. Each degenerate primer sequence corresponds to many different sequences all sharing the same constant nucleotides at constant positions and representing all possible variations of the N positions.

A tag or tag sequence is a selected nucleic acid with a specified nucleic acid sequence. A tag probe has a region that is complementary to a selected tag. A set of tags or a collection of tags is a collection of specified nucleic acids that may be of similar length and similar hybridization properties, for example similar $T_m$. The tags in a collection of tags bind to tag probes with minimal cross hybridization so that a single species of tag in the tag set accounts for the majority of tags which bind to a given tag probe species under hybridization conditions. For additional description of tags and tag probes and methods of selecting tags and tag probes see U.S. Ser. No. 08/626,285 and EP/0799897, each of which is incorporated herein by reference in their entirety.

A collection of capture probes may be designed to interrogate a collection of target sequences. The collection would comprise at least one capture probe for each target sequence to be amplified. There may be multiple different capture probes for a single target sequence in a collection of capture probes, for example, there may be a capture probe that hybridizes to one strand of the target sequence and a capture probe that hybridizes to the opposite strand of the target sequence, these may be referred to as a forward locus or target specific primer and a reverse locus or target specific primer. There also may be two or more capture probes that hybridize at different locations downstream of the target sequence.

A collection of capture probes may be used to amplify a subset of a genome. The collection of capture probes may be initially used to generate a copy of the target sequences in the genomic sample and then the copies may be amplified using common primers. The amplification may be done simultaneously in the same reaction and often in the same tube.

The term "target sequence", "target nucleic acid" or "target" refers to a nucleic acid of interest. The target sequence may or may not be of biological significance. As non-limiting examples, target sequences may include regions of genomic DNA which are believed to contain a polymorphism. The number of sequences to be interrogated can vary, but preferably are from about 1000, 2,000, 5,000, 10,000, 20,000 or 100,000 to 5000, 10,000, 100,000, 1,000,000 or 3,000,000 target sequences.

An "array" comprises a support, preferably solid, with nucleic acid probes attached to the support. Preferred arrays typically comprise a plurality of different nucleic acid probes that are coupled to a surface of a substrate in different, known locations. These arrays, also described as "microarrays" or colloquially "chips" have been generally described in the art, for example, U.S. Pat. Nos. 5,143,854, 5,445,934, 5,744,305, 5,677,195, 5,800,992, 6,040,193, 5,424,186 and Fodor et al., Science, 251:767-777 (1991). Each of which is incorporated by reference in its entirety for all purposes.

Arrays may generally be produced using a variety of techniques, such as mechanical synthesis methods or light directed synthesis methods that incorporate a combination of photolithographic methods and solid phase synthesis methods. Techniques for the synthesis of these arrays using mechanical synthesis methods are described in, e.g., U.S. Pat. Nos. 5,384,261, and 6,040,193, which are incorporated herein by reference in their entirety for all purposes. Although a planar array surface is preferred, the array may be fabricated on a surface of virtually any shape or even a multiplicity of surfaces. Arrays may be nucleic acids on beads, gels, polymeric surfaces, fibers such as fiber optics, glass or any other appropriate substrate. (See U.S. Pat. Nos. 5,770,358, 5,789,162, 5,708,153, 6,040,193 and 5,800,992, which are hereby incorporated by reference in their entirety for all purposes.)

A genotyping array comprises probes that are specific for one allele of a polymorphism. Genotyping arrays are described, for example, in U.S. patent application Ser. Nos. 10/264,945 and 10/442,021 and U.S. Provisional patent applications Nos. 60/470,475 filed May 14, 2003, 60/483,050 filed Jun. 27, 2003 and 60/417,190 filed Oct. 8, 2002, each of which is incorporated herein by reference in its entirety.

Arrays may be packaged in such a manner as to allow for diagnostic use or can be an all-inclusive device; e.g., U.S. Pat. Nos. 5,856,174 and 5,922,591 incorporated in their entirety by reference for all purposes.

Preferred arrays are commercially available from Affymetrix under the brand name GeneChip® and are directed to a variety of purposes, including genotyping and gene expression monitoring for a variety of eukaryotic and prokaryotic species. (See Affymetrix Inc., Santa Clara and their website at affymetrix.com.) A genotyping array such as the Human Mapping Array 10K Xba 131 may be used to determine the genotype of a collection of SNPs by hybridization. The array contains probes that are specific for each possible allele for a collection of SNPs. Fragments that carry the SNPs are amplified, labeled and hybridized to the array. The presence of a fragment is determined by the hybridization pattern. For additional description of a genotyping array see U.S. provisional patent application No. 60/417,190 filed Oct. 8, 2002.

Combinatorial chemistry may be used for the parallel synthesis of discreet compounds, for example, oligonucleotides of different sequence on a solid support. See, for example, U.S. Pat. Nos. 5,412,087, 5,424,186, 5,445,934 and 6,040,193 which are each incorporated herein by reference. Many different compounds may be synthesized. The compounds may be oligonucleotides which may be synthesized on a solid support so that each discreet compound or oligonucleotide is localized to a specific region, or feature, of the array which may be predefined. In some embodiments there may be overlap between regions. In some embodiments a plurality of different oligonucleotides are generated, each sharing a core set of bases but differing at some positions. For example, each feature of the array may be of the sequence 5'-GAAT-NNCNG-3' and within each discreet feature the N's will be the same, for example one feature may be 5'-GAATcgCtG-3' while another feature may be 5'-GAATttCgG-3'. The core bases are GAAT-C-G. The synthesis of many different probes may be accomplished in this manner with increase efficiency and decreased cost because the majority of probes of the array have the same core set of bases and addition of those bases may be done en masse without the use of feature specific photolithography, i.e. all features may be activated simultaneously for those positions. In some embodiments there are control oligonucleotides on the array that may or may not share the common core bases.

Hybridization probes are oligonucleotides capable of binding in a base-specific manner to a complementary strand of nucleic acid. Such probes include peptide nucleic acids, as described in Nielsen et al., Science 254, 1497-1500 (1991), and other nucleic acid analogs and nucleic acid mimetics. See U.S. Pat. No. 6,156,501.

The term hybridization refers to the process in which two single-stranded polynucleotides bind non-covalently to form a double-stranded polynucleotide; triple-stranded hybridization is also theoretically possible. The resulting double-stranded polynucleotide is a "hybrid." The hybrid may have double-stranded regions and single stranded regions.

Hybridizations are usually performed under stringent conditions, for example, at a salt concentration of no more than 1 M and a temperature of at least 25° C. For example, conditions of 5×SSPE (750 mM NaCl, 50 mM NaPhosphate, 5 mM EDTA, pH 7.4) and a temperature of 25-30° C. are suitable for allele-specific probe hybridizations. For stringent conditions, see, for example, Sambrook et al., (2001) which is hereby incorporated by reference in its entirety for all purposes above.

An individual is not limited to a human being, but may also include other organisms including but not limited to mammals, plants, bacteria or cells derived from any of the above.

(C) Multiplexed Locus Specific Genotyping

Generally, the invention provides methods for highly multiplexed locus specific amplification of nucleic acids and methods for analysis of the amplified products. In preferred embodiments the amplified targets prepared using Multiplexed Anchored Runoff Amplification (MARA) are analyzed to determine the genotype of SNPs. In some embodiments the invention combines the use of capture probes that comprise a common sequence and a locus-specific region with adaptor-modified sample nucleic acid; the adaptor comprises a second common sequence. The capture probes are extended to produce copies of the sample DNA that contain common priming sequences flanking the target sequence. The copies are amplified with a generic set of primers that recognize the common sequences. The amplified product may be analyzed by hybridization to an array of probes.

In one embodiment the steps of the invention comprise: designing and synthesizing capture probes; digesting a nucleic acid sample; ligating adaptors to the fragmented sample; mixing the fragments and the capture probes under conditions that will allow hybridization of the fragments and the capture probes; extending the capture probes in the presence of dNTPs and polymerase; amplifying the extended capture probes using primers to the common sequences in the capture probe and the adaptor; and detecting the presence or absence of target sequences of interest. In a preferred embodiment allele discrimination is achieved by hybridization to high density DNA oligonucleotide arrays.

One embodiment of the methods is illustrated in FIG. 1. Capture probes are designed with a locus specific region ($LS1_F$ and $LS1_R$) that hybridizes near a target sequence of interest and a common sequence (A1) that is 5' of the locus specific region.

The common priming site may be present in a plurality of capture probes so that a primer to A1 may be used for amplification of a plurality of different targets in subsequent steps. The capture probes may be attached to a solid support so that they have a free 3' end or the extension may be done in solution. A plurality of a single species of capture probe may be synthesized at a discreet location on an array and may form a discrete feature of an array. Each feature of the array may contain a different species of locus specific capture probe at a known or determinable location.

Genomic DNA is fragmented and adaptors comprising a second common sequence (A2) are ligated to the fragments. The adaptor-ligated fragments are then mixed with the capture probes under conditions that allow hybridization of the fragments to the capture probes on the array. The capture probes are then extended using the adaptor-ligated fragments as template. The extension product has a common sequence, A1, near its 5' end and a second common sequence A2 near its 3' end. These common sequences flank a region of interest. The capture probes are then released from the array and extended capture probes are amplified by PCR using primers to the common sequences A1 and A2. The amplified product may then be analyzed by, for example, hybridization to an array. Information about the region of interest can be determined by analysis of the hybridization pattern.

Figure 2:
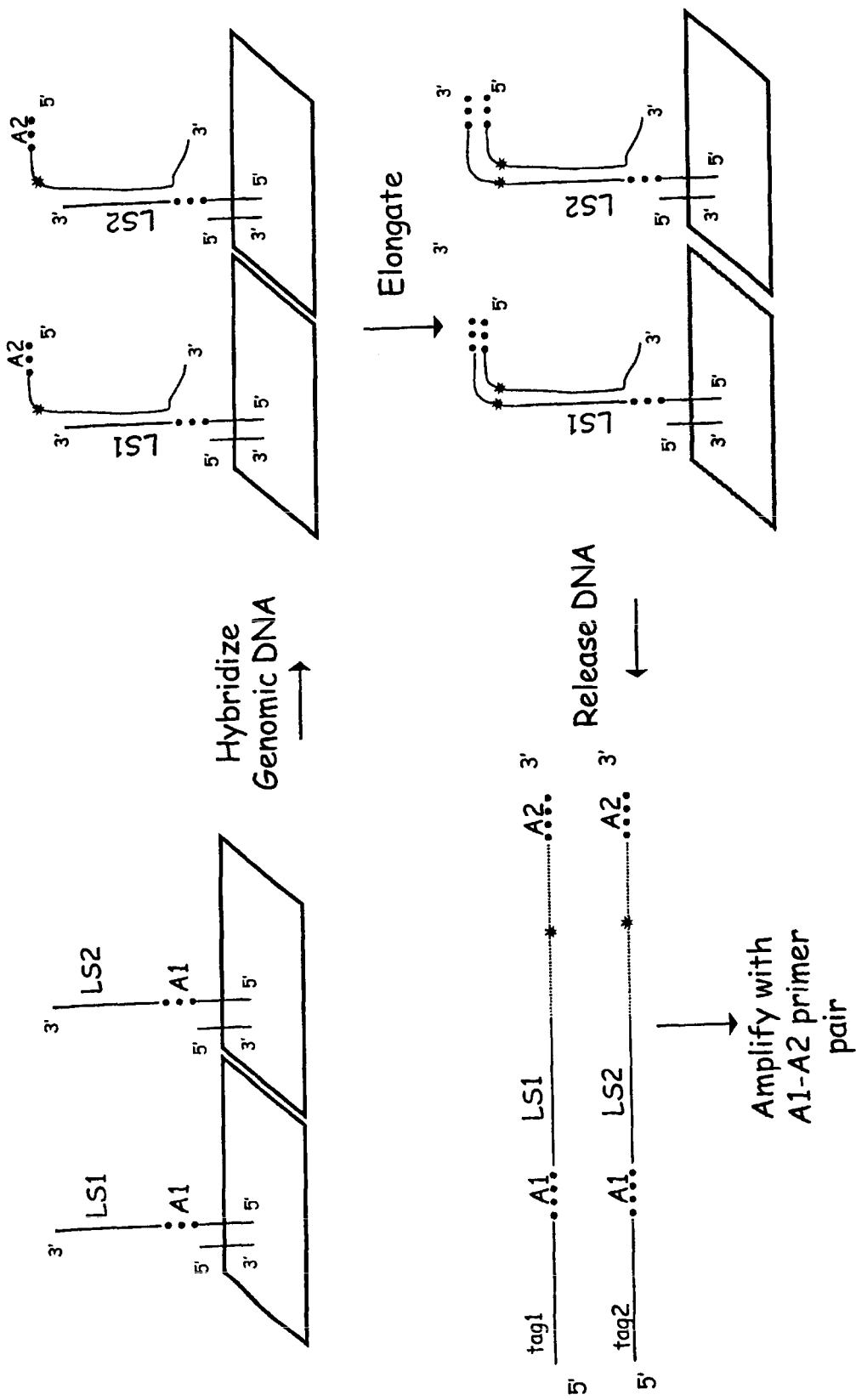
FIG. 2 shows a method where the capture probes are attached to a solid support by hybridization to a probe that is covalently attached to the solid support. The probes on the array are complementary to a tag sequence in the 5' region of the capture probe. The capture probe hybridizes so that the 3' end is available for extension.

A second embodiment of the methods is illustrated in FIG. 2. Capture probes are designed with a locus specific region (LS1 or LS2) and a common sequence (A1) as in FIG. 1. In this embodiment the capture probes further comprise a tag sequence that is unique for each species of capture probe designed. (For a description of tags and tag probes, see, U.S. Ser. No. 08/626,285.) The capture probes are attached to the array through hybridization of the tag sequence to a substantially complementary tag probe sequence that is attached to the array. The tag probes may be attached to the array in discrete locations. Different species of tag probes are present at different discrete, spatially addressable locations. Adaptor-ligated genomic DNA is hybridized to the array so that the capture probes hybridize to target sequences in the sample. The capture probes are extended as in FIG. 1 to incorporate the target sequence and common sequence A2. The extended capture probes are released and amplified using primers A1 and A2. The amplified product may then be analyzed by, for example, hybridization to an array. Information about the region of interest can be determined by analysis of the hybridization pattern. The amplified sample may be analyzed by any method known in the art, for example, MALDI-TOF mass spec, capillary electrophoresis, OLA, dynamic allele specific hybridization (DASH) or TaqMan® (Applied Biosystems, Foster City, Calif.). For other methods of genotyping analyses see Syvanen, *Nature Rev. Gen.* 2:930-942 (2001) which is herein incorporated by reference in its entirety.

In some embodiments the capture probes are attached to a solid support prior to hybridization and hybridization takes place while the capture probes are attached to the solid support. In some embodiments the capture probes are synthesized on a solid support. Any suitable solid support known in the art may be used, for example, arrays, beads, microparticles, microtitre dishes and gels may be used. In some embodiments the capture probes are synthesized on an array in a 5' to 3' direction.

In some embodiments hybridization and extension of capture probes are done while the capture probes are attached to a solid support. Following extension of the capture probes nucleic acids that are not covalently attached to the solid support may be washed away. In some embodiments the extended capture probes are released from the solid support prior to amplification. In another embodiment amplification takes place while the extended capture probes are attached to the solid support. The extended capture probes may be released from the solid support by, for example, using a reversible linker or an enzymatic release, such as an endonuclease or by a change in conditions that results in disruption of an interaction between the capture probe and the solid support, for example, when capture probes are associated with the solid support through base pairing between a tag in the capture probe and a tag probe on the solid support, disruption of the base pairing interaction releases the capture probes from the solid support. Enzymatic methods include, for example, use of uracil DNA glycosylase (UDG) or (UNG). UNG catalyzes the hydrolysis of DNA that contains deoxyuridine at the site the uridine is incorporated. Incorporation of one or more uridines in the capture probe followed by treatment with UNG will result in release of the capture probe from the solid support. A thermolabile UNG may also be used.

In preferred embodiments a collection of target sequences is analyzed. A plurality of capture probes is designed for a plurality of target sequences. Pools of more than 250, more than 750, more than 1,000 or more than 4,000 different capture probes may be simultaneously extended in a multiplexed reaction. In some embodiments target sequences contain or are predicted to contain a polymorphism, for example, a SNP. The polymorphism may be, for example, near a gene that is a candidate marker for a phenotype, useful for diagnosis or a disorder or for carrier screening or the polymorphism may define a haplotype block (see, Daly et al. *Nat. Genet.* 29:229-32 (2001), and Rioux et al. *Nat. Genet.* 29:223-8 (2001) and U.S. patent application Ser. No. 10/213,272, each of which is incorporated herein by reference in its entirety). A collection of capture probes may be designed so that capture probes hybridize near a polymorphism, for example, within 1, 5, 10, or 100 to 5, 10, 100, 1000, 10,000 or 100,000 bases from the polymorphism. The capture probes hybridize to one strand of the target sequence and can be extended through the polymorphic site or region so that the extension product comprises a copy of the polymorphic region.

Many amplification methods are most efficient at amplification of smaller fragments. For example, PCR most efficiently amplifies fragments that are smaller than about 2 kb (see, Saiki et al. 1988). In one embodiment capture probes and fragmentation conditions are selected for efficient amplification of a selected collection of target sequences. The size of the amplified fragments is dependent on where the target specific region of the capture probe hybridizes to the target sequence and the 5' end of the fragment strand that the capture probe is hybridized to. In some embodiments of the present methods capture probes and fragmentation methods are designed so that the target sequence of interest can be amplified as a fragment that is, for example, less than 20,000, 2,000, 1,000, 800, 500, 400, 200 or 100 base pairs long. Multiplex PCR methods and methods to improve PCR amplification have been shown. See for example, Edwards and Gibbs *PCR Methods Appl* 3: S65-75 (1994), Henegariu, et al. *Biotechniques* 23: 504-511 (1997), Shuber et al. *Genome Res* 5: 488-493 (1995), Broude, et al. *Antisense Nucleic Acid Drug Dev* 11: 327-332 (2001), Broude, et al. *Proc Natl Acad Sci USA* 98: 206-211 (2001) and Brownie, et al. *Nucleic Acids Res* 25: 3235-3241 (1997).

For multiplexed amplification capture probes can be designed so that the 3' end of the target specific region hybridizes to the base that is immediately 3' of a position to be interrogated in the target sequence. For example, if the sequence to be interrogated is a polymorphism and the sequence is 5'-GCTXATCGG-3', where X is the polymorphic position, the target specific region of the capture probe may have the sequence 5'-CCGAT-3'. When the sample is fragmented with site specific restriction enzymes the length of the fragments will also depend on the position of the nearest recognition site for the enzyme or enzymes used for fragmentation. A collection of target sequences may be selected based on proximity to restriction sites. In some embodiments target sequences are selected for amplification and analysis based on the presence of a sequence of interest, such as a SNP, and proximity to a cleavage site for a selected restriction enzyme. For example, SNPs that are within 200, 500, 800, 1,000, 1,500, 2,000 or 20,000 base pairs of either a restriction site, such as, for example, an EcoRI site, a BglI site, an XbaI site, a NotI site or any other restriction enzyme site may be selected to be target sequences in a collection of target sequences. Preferably the sequence to be interrogated, for example the polymorphic position, is between the target specific sequence of the capture probe and the downstream restriction site.

In another embodiment a fragmentation method that randomly cleaves the sample into fragments that are 30, 100, 200, 500 or 1,000 to 100, 200, 500, 1,000 or 2,500 base pairs on average may be used. Fragmentation may occur before or after extension of capture probes. When fragmentation is performed prior to extension of capture probes an adaptor may be ligated to the fragments. Fragments may be blunt ended and a blunt end adaptor may be ligated. When the capture probe is extended the adaptor sequence will be incorporated. If fragmentation is performed after capture probe extension an adaptor may be ligated to the end of the extended capture probe to incorporate a primer binding site.

Figure 3:
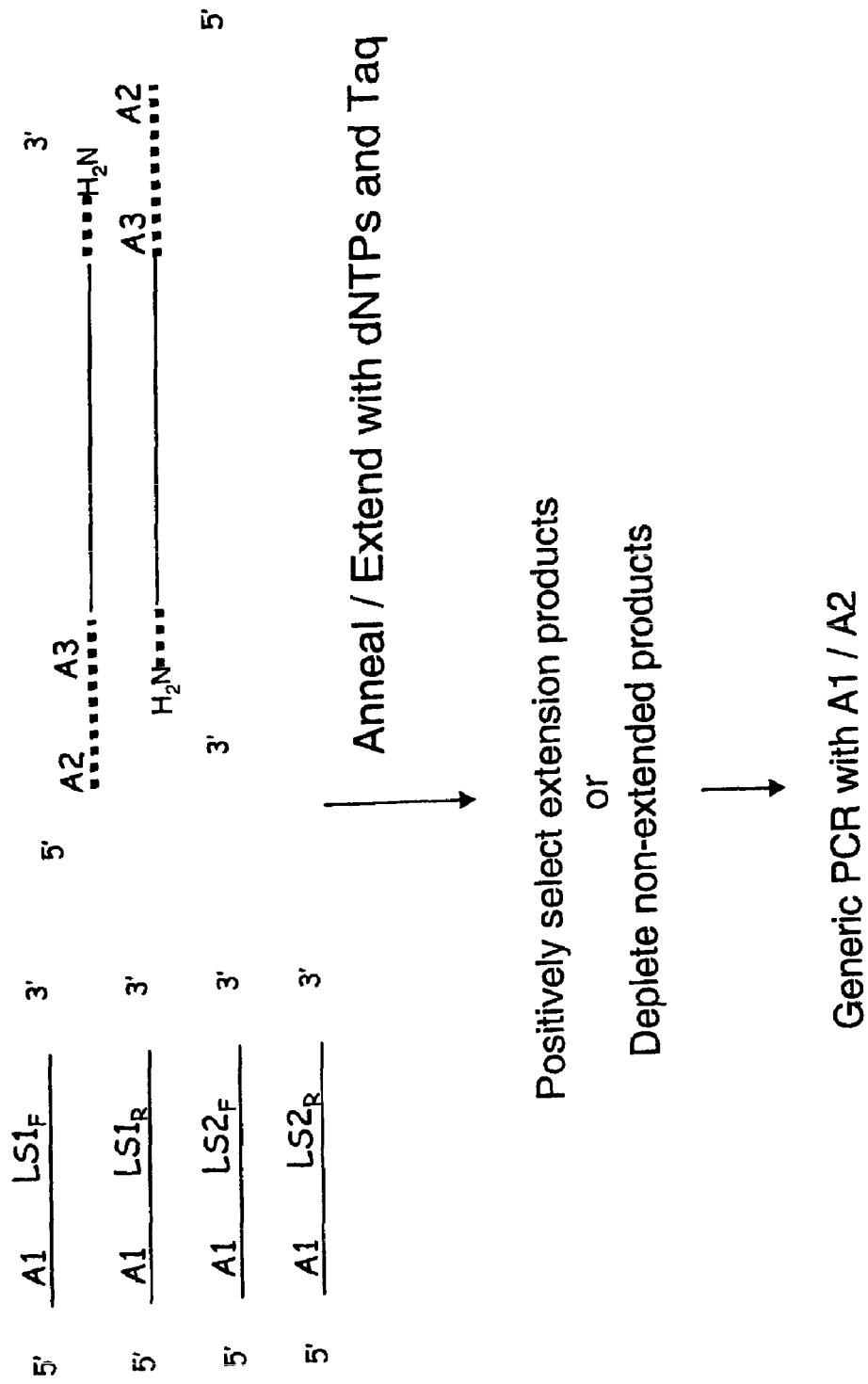
FIG. 3 shows a schematic of solution-based multiplexed SNP genotyping. A sample is fragmented and ligated to an adaptor so that the adaptor sequence that hybridizes to the 3' end of the strands of the fragments is blocked from extension. Locus specific capture probes are hybridized to the fragments and extended in solution then amplified by PCR using primers to A1 and A2. Prior to amplification the extended capture probes may be enriched by, for example, removal of non-extended products or by positive selection of extended products.

In another embodiment, illustrated in FIG. 3, the capture probes are in solution and hybridization and extension take place in solution. In this embodiment the nucleic acid sample is fragmented and adaptor containing common sequences A2 and A3 is ligated to the fragments. In some embodiments one strand of the adaptor, the strand that is ligated to the 3' end of the fragment strands lacks common sequence A2 and is blocked from extension at the 3' end. Ligation of the blocked adaptor strand to the 3' end of the fragment strands prevents the fragments from being extended to incorporate A2 at both ends, thus preventing amplification of the fragments by primer A2 in the subsequent PCR amplification step. Capture probes with locus specific regions and common sequence A1 are mixed with the adaptor-ligated fragments under conditions that allow hybridization of the capture probes to the adaptor ligated fragments. The capture probes are extended in the presence of polymerase and dNTPs. In some embodiments the extended capture probes are positively selected to generate a sample that is enriched for extended capture probes. In another embodiment extended capture probes are enriched by depleting non-extended products.

MARA primers with Degenerate Locus Specific Region. Many of the disclosed methods, as well as many other genotyping methods, utilize primers comprising locus specific regions. As the number of polymorphisms to be genotyped increases so does the number of locus specific primers that must be synthesized. Synthesis of large numbers of locus specific primers by standard methods can be cost prohibitive. Handling large numbers of individually aliquoted locus specific primers, for example in 96 well plates, may also be difficult and errors may be introduced, for example putting the wrong primer in the wrong well or mixing primers in a well. Synthesis of locus specific primers directly on a solid support may be used to simplify and reduce the cost of synthesizing large numbers of locus specific oligonucleotides. Combinatorial synthesis of locus specific primers, for example, MARA capture probes, with degenerate positions may also improve efficiency and reduce the cost of locus specific genotyping applications. The degenerate capture probes may be synthesized by any method known, for example on a solid support such as on an array or on beads. Methods for combinatorial synthesis are described in U.S. Pat. No. 5,541,061. Degenerate-oligonucleotide-primed PCR methods have been described in Telenius et al. *Genomics* 13:718-725 (1992).

Figure 4:
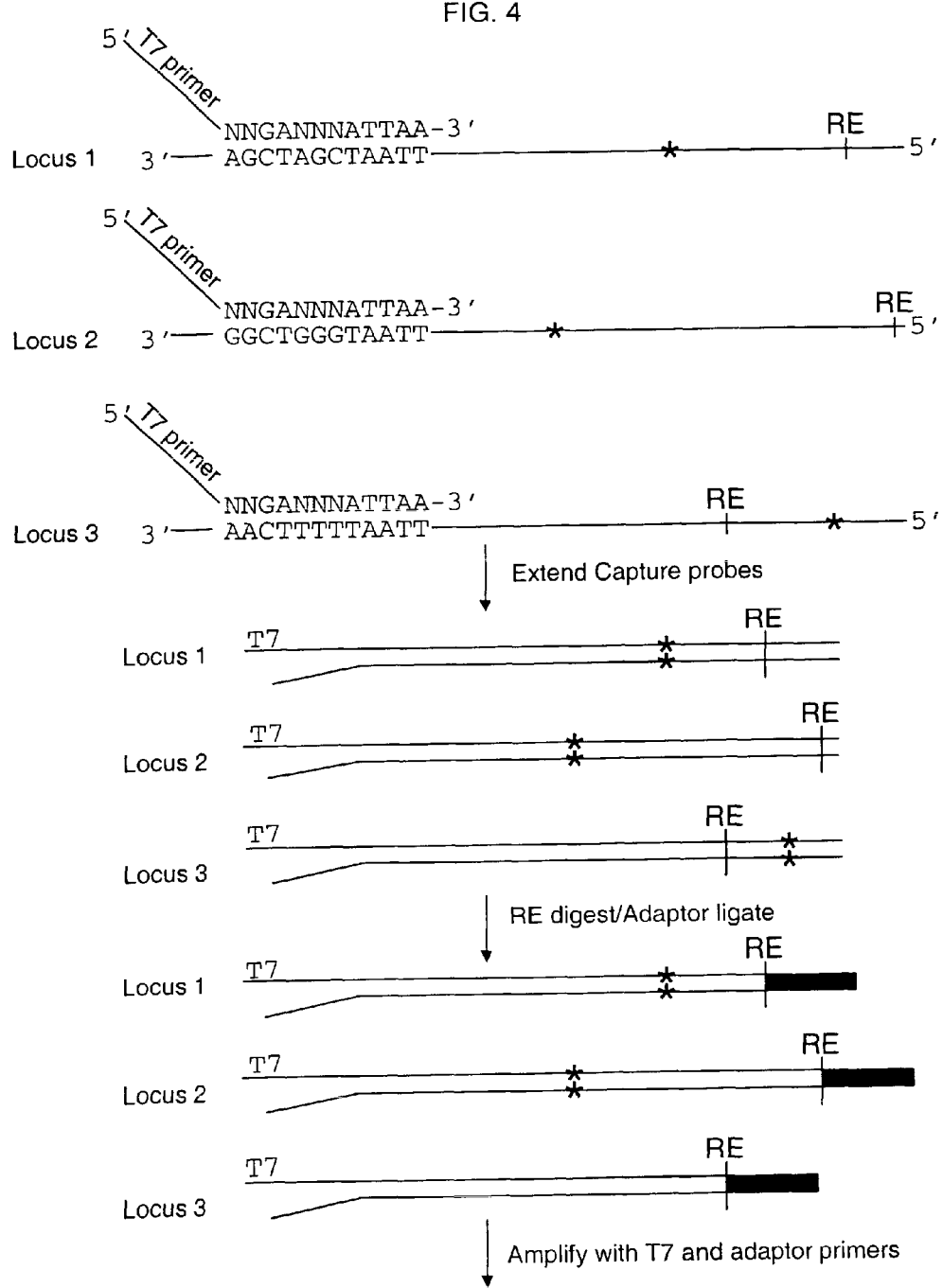
FIG. 4 shows amplification of multiple loci with a degenerate capture probe. A capture probe with degenerate positions (indicated by N) and constant positions (indicated by G, A and T) is shown hybridizing to three different loci, (locus 1, 2 and 3). The degenerate capture probe also has a 5' common region which is the T7 promoter primer sequence. The three loci have a polymorphism (*) and a NotI restriction site. The capture probes are hybridized to the target sequences and extended. The extended products are digested with NotI and adaptors are ligated to the ends. The fragments are then amplified with primers to the adaptor and to the T7 sequence.
Figure 5A:
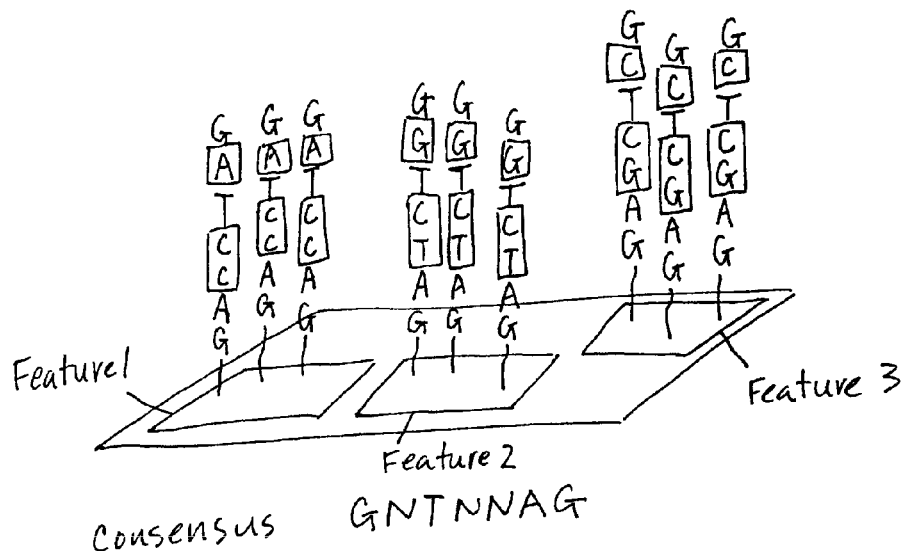
FIG. 5A shows an array of probes where the majority of the probes in a feature have the same sequence and a plurality of the features is designed have a common core sequence. Each feature of the array has the sequence GNTNNAG and the N's are the same within a feature and different between features.
Figure 5B:
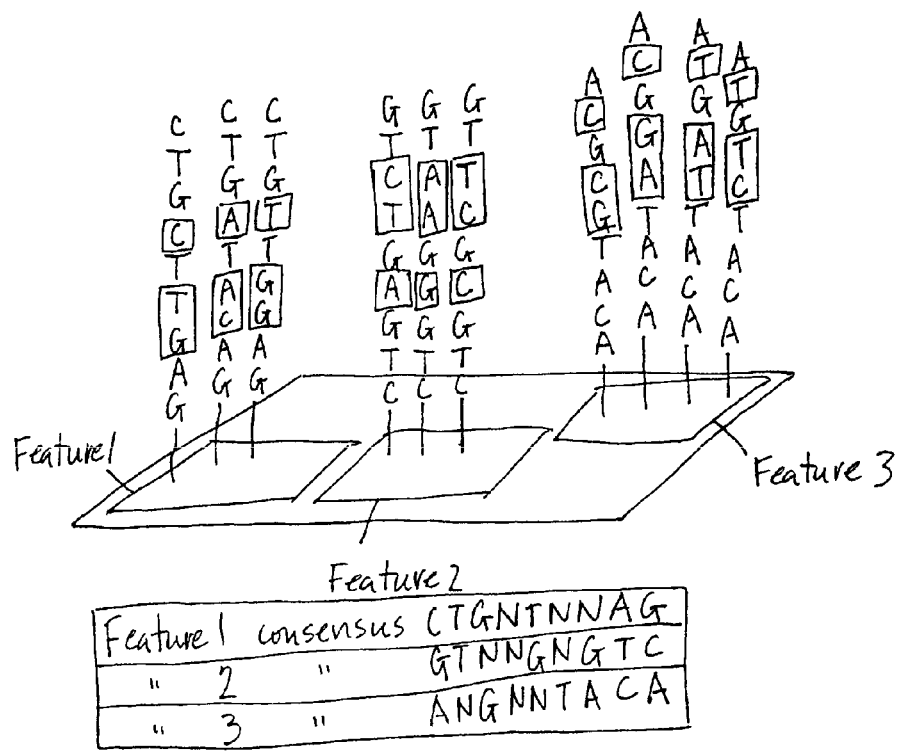
FIG. 5B shows an array of probes where the probes in a feature have the same core sequence but are different at some positions and the different features have different core sequences. Feature 1 has the core sequence GTGNTNNAG, feature 2 has the core sequence GTNNGNGTC and feature 3 has the core sequence ANGNNTACA.

MARA capture probes may be designed so that the locus specific region of a plurality of primers share some common sequence features. In one embodiment polymorphisms are selected for genotyping based on the presence of common sequence motifs. For example, polymorphisms may be selected that are within 100, 200, 500, or 1000 base pairs of a selected common sequence of 4, 5, 6, 8 or 10 bases, the selected sequence may be, for example, a restriction enzyme recognition site. The polymorphisms are then analyzed to identify a subset that also shares a consensus sequence immediately upstream of the selected common sequence. The consensus sequence may be for example a stretch of 8-20 bases. Some of the bases are identical for each polymorphism in the subset and some of the bases vary from one polymorphism to the next. An example of this is illustrated in FIG. 4. The three loci share a consensus sequence upstream of a polymorphism. The common sequence shared by each is ATTAA and the similar sequence is GANNN immediately upstream of the ATTAA. The same partially degenerate primer with locus specific sequence 5' NNGANNNATTAA 3' (SEQ ID NO. 4), can be hybridized to each of the three loci and extended.

In a preferred embodiment the locus specific region of at least some of the capture probes contains degenerate positions. An oligonucleotide pool may be synthesized so that some positions are a single fixed nucleotide and some positions can be one of two or more different nucleotides. For example the sequence of the locus specific region of some of the oligonucleotides may be 5'-NNGANNNATTAA-3', where N can be any nucleotide, including G, C, A and T. There are $4^5$ or 1024 different sequences possible for this oligonucleotide if N is either G, C, A or T. Each of the 1024 sequences may occur at many places in the genome. Assuming random distribution of sequences any given 12 mer should occur approximately 180 times in the 3 billion base pair human genome ($4^{12}$ is ~$1.7 \times 10^7$ and $3 \times 10^9 / 1.7 \times 10^7$ is ~180). A plurality of SNPs may be assayed using a single degenerate pool of oligonucleotides. If each of the 1024 sites is present 180 times in the genome, a single degenerate oligonucleotide synthesis could hybridize and serve as a primer at ~180,000 different sites (1024×180 is 184,320). A plurality of the capture probes share common sequences separated by variable sequences. For example, in FIG. 4 the locus 1, 2 and 3 priming sites share the sequence NNCTNNNTAATT where the underlined nucleotides are common between each of the three sites and the nucleotides indicated by N are variable. An oligonucleotide that is degenerate at each of the N positions and has the common sequences could be used to amplify each of the three loci.

In one embodiment combinatorial chemistry is used to synthesize a pool of capture probes. The use of combinatorial chemistry allows a large number of oligonucleotides of different sequence to be synthesized en masse at a reduced cost. In one embodiment some positions in the oligonucleotides will be defined and some will be variable. In some embodiments the capture probes are synthesized on an array and some positions of at least some of the oligonucleotides are variable. The inclusion of a variable position allows for the synthesis of multiple different oligonucleotides at a single feature of the array. Capture probes may be synthesized on a solid support at distinct positions or features using, for example photolithography or printing methods. The variable positions may be at the same location in all of the features or at different locations that vary from feature to feature. For example, all of the probes of the array may have variable positions at positions 5, 10, 11, and 15-20 or some of the features may have variable positions at these positions and some may have variable positions at other positions that are different from these, for example at 5, 12-16 and 22. The probes may be synthesized on an array as disclosed in U.S. Pat. No. 5,412,087 and the method of synthesis may be designed to minimize steps and cost by, for example, the methods disclosed in U.S. Pat. No. 5,593,839.

Methods of combinatorial synthesis of polymer libraries have been described in U.S. Pat. No. 5,541,061. A large number of different sequence probes may be synthesized in a series of pooled and separate synthesis steps so that a large number of different polymers may be synthesized in a reduced number of steps. Pools of probes can be synthesized so that all of the probes in a given pool share common sequence elements and vary at similar positions. The pools of probes can be efficiently synthesized in a reduced number of steps by using pooled and unpooled synthesis steps.

In one embodiment a collection of SNPs is first selected for genotyping. Capture probes are then designed for the collection of SNPs. Each SNP to be genotyped is analyzed to identify a common sequence near the SNP, for example, a restriction enzyme recognition site. In one embodiment the common sequence is within 1000 or 2000 base pairs of the polymorphism. The sequence surrounding the common sequence is then analyzed and compared to the sequence surrounding that common sequence in other SNPs of the collection to identify a subset of SNPs that have additional common sequences surrounding the first common sequence (see FIG. 6). Degenerate primers are designed that have constant sequences at positions that are common among the SNPs in the subset. These steps may be repeated for other subsets so that a single degenerate capture probe can be used for each identified subset of SNPs.

Figure 6A:
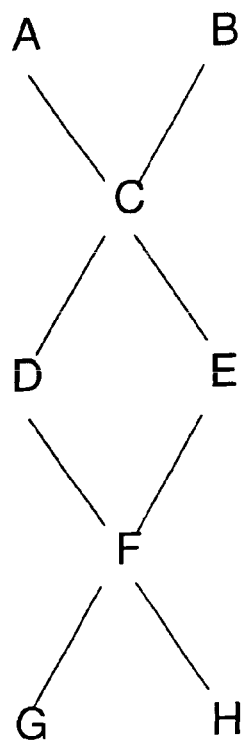
FIG. 6A shows combinatorial methods that include separate and pooled monomer addition steps.
Figure 6B:
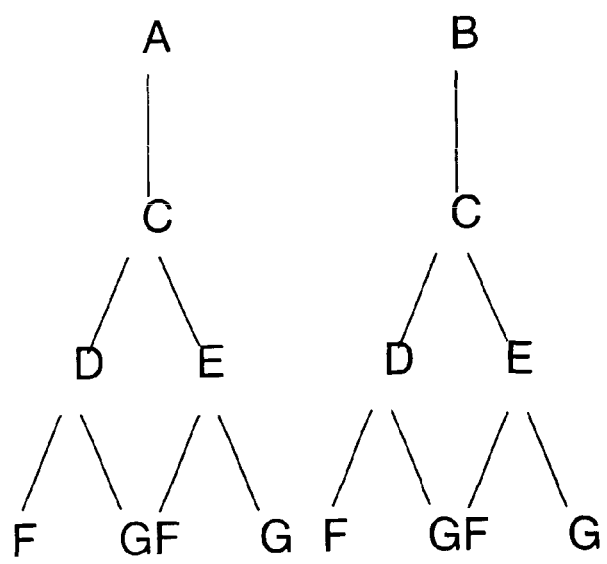
FIG. 6B shows synthesis without the use of pooled monomer addition steps.

In another embodiment a pool of locus specific capture probes is synthesized using combinatorial chemistry methods as disclosed in U.S. Pat. No. 5,541,061. Capture probes are synthesized in pools using a series of separate and pooled monomer addition steps. The use of separate and pooled steps allows a larger number of different locus specific probes to be synthesized using fewer steps. For example, FIG. 6A shows a schematic of a combinatorial synthesis process. In the first step monomers A and B are added separately, then they are pooled and C is added, the sample is separated and D and E are added, then pooled and F is added and finally G and H are added to separate pools. The final result is two pools each with 4 different polymers, (ACDFG, ACEFG, BCDFG, BCEFG and ACDFH, ACEFH, BCDFH, BCEFH). This requires 8 separate addition steps. FIG. 6B shows that if each monomer was added separately it would require 16 steps to synthesize the same 16 polymers. A plurality of capture probes may be designed to interrogate a plurality of SNPs and the probes may be synthesized in pools using a combinatorial synthesis strategy.

In one embodiment a collection of SNPs to be genotyped is identified and a collection of capture probes is designed so that a minimum number of probes may be synthesized to genotype the collection of SNPs. Some of the capture probes may be synthesized to genotype a specific SNP and some capture probes may be synthesized to include degenerate positions so that a single synthesis may be used to generate multiple different capture probes that are each specific for a SNP. In some embodiments the capture probes also have a common sequence, such as a T7 promoter sequence, that may be used as a primer binding site so that a common primer may be used to amplify extension products. For example, the pool of capture probes may comprise 5'TAATACGACTCACTAT-AGGGAGAACNNGTNNNNAATT-3' (SEQ ID NO. 5). The pool of degenerate capture probes will bind to many sites within the genome.

In one embodiment the degenerate capture probes are hybridized to the targets and extended using the target as template. The extended probes may be digested with a restriction enzyme that may cut within 200, 500 or 1000 bp of the capture probe binding site but not between the polymorphism to be detected and the capture probe binding site. Digestion may be done before extension so that the double stranded target is digested or after extension so that the extended capture probe-target duplex is digested. After digestion, adaptors may be ligated to the overhang. The adaptor may have a common priming sequence. After extension and adaptor ligation the products may be amplified with a T7 primer and a primer complementary to the ligated adaptor.

In one embodiment a collection of degenerate locus specific primers is designed to hybridize near a polymorphism so that the polymorphism is between the site of primer binding and a restriction site. In one embodiment polymorphisms and priming sites are selected so that the distance between the restriction site and the primer binding site is within 200, 500, 1000 or 2000 base pairs. In some embodiments the distance is less than about 5,000 or less than about 10,000 base pairs. In one embodiment each degenerate locus specific primer has a common priming sequence at the 5' end and a degenerate sequence near the 3' end. In one embodiment the degenerate locus specific primer also has a tag sequence which may be between the common priming sequence and the degenerate sequence.

In one embodiment polymorphisms to be analyzed are selected to have the following criteria: the polymorphism is located near a potential priming site (the priming site is where the capture probe hybridizes) for a selected degenerate capture probe, for example, within 500, 1000, 2000, 5000 or 10,000 base pairs of the priming site; a selected restriction site is located near the polymorphism, for example, within 500, 1000, 2000, 5000 or 10,000 base pairs of the polymorphism; and the polymorphism is between the priming site and the restriction site. In one embodiment a plurality of polymorphisms are identified which meet these criteria for a single degenerate capture probe and a single restriction enzyme. For example, a plurality of polymorphisms may be identified that are within 500 base pairs of a degenerate priming site for the following sequence: 5'-ACNNGTNNNNAATT-3' (SEQ ID NO. 1) and within 500 base pairs of a NotI site so that the polymorphism is between the NotI site and the priming site.

In one embodiment two or more collections of target sequences that vary in the common or consensus sequence may be simultaneously analyzed. The polymorphisms to be analyzed may each be near one of two or more degenerate locus specific priming sites. The sites may vary in the common sequence, for example. Two or more separate pools of capture probes may be synthesized and used for MARA.

In one embodiment genomic DNA is digested with a restriction enzyme and ligated to an adaptor. The adaptor has a common priming site that may be different from the common priming site in the degenerate capture probe. The adaptor ligated genomic DNA and the degenerate capture probes are mixed under conditions that allow hybridization of the degenerate capture probes to corresponding priming sites in the adaptor ligated genomic DNA. The degenerate capture probes are then extended so that the complement of the adaptor sequence is incorporated into the extended degenerate capture probes. The extended degenerate capture probes are then amplified by, for example, PCR using primers to the common priming site from the adaptor and the common priming site in the degenerate capture probes. See, FIG. 4. The amplified MARA product may then be analyzed to determine the genotype of the one or more SNPs present. In one embodiment an array of probes is designed to genotype SNPs predicted to be present in the MARA product.

Feature specific degenerate probes may be synthesized. The probes may be synthesized on an array using combinatorial chemistry such that each feature has a unique sequence but all of the features share some common sequence. The synthesis steps for the common sequence do not require a mask since all of the probes have the same base at that position. For example if the degenerate sequence is 5'-GTTNCN-NAT -3' all of the probes would have the GTT-C-AT sequence and addition of these bases could be done en masse without a photolithography step. The probes at different features would vary at the N positions but within a feature most probes would have the same base at a given N position.

In many embodiments of the present methods one or more enrichment step may be included to generate a sample that is enriched for extended capture probes prior to amplification with common sequence primers. In some embodiments it is desirable to separate extended capture probes from fragments from the starting nucleic acid sample, adaptor-ligated fragments, adaptor sequences or non-extended capture probes, for example. In one embodiment the capture probes are extended in the presence of a labeled dNTP, for example dNTPs labeled with biotin. The labeled nucleotides are incorporated into the extended capture probes and the labeled extended capture probes are then separated from non-extended material by affinity chromatography. When the label is biotin the labeled extended capture probes can be isolated based on the affinity of biotin for avidin, streptavidin or a monoclonal anti-biotin antibody. In one embodiment the antibody may be coupled to protein-A agarose, protein-A sepharose or any other suitable solid support known in the art. Those of skill in the art will appreciate that biotin is one label that may be used but any other suitable label or a combination of labels may also be used, such as fluorescein which may be incorporated in the extended capture probe and an anti-fluorescein antibody may be used for affinity purification of extended capture probes. Other labels such as, digoxigenin, Cyanine-3, Cyanine-5, Rhodamine, and Texas Red may also be used. Antibodies to these labeling compounds may be used for affinity purification. Also, other haptens conjugated to dNTPs may be used, such as, for example, dinitrophenol (DNP).

In another embodiment capture probes that have been extended through the adaptor sequence on the adaptor modified DNA are made double stranded by hybridizing and extending a primer. Only the fully extended capture probes will have the priming site so partially extended capture probes will remain single-stranded. The sample is then digested with a nuclease that selectively digests single stranded nucleic acid, such as E. Coli Exonuclease I. The sample is then amplified.

In another embodiment extension products may be enriched by circularization followed by digestion with a nuclease such as Exonuclease VII or Exonuclease III. The extended capture probes may be circularized, for example, by hybridizing the ends of the extended capture probe to an oligonucleotide splint so that the ends are juxtaposed and ligating the ends together. The splint will hybridize to sequences in the extended capture probe and bring the 5' end of the capture probe next to the 3' end of the capture probe so that the ends may be ligated by a ligase, for example DNA Ligase or Ampligase Thermostable DNA. See, for example, U.S. Pat. No. 5,871,921 which is incorporated herein by reference. The circularized product will be resistant to nucleases that require either a free 5' or 3' end.

A variety of nucleases may be used in one or more of the embodiments. Nucleases that are commercially available and may be useful in the present methods include: Mung Bean Nuclease, E. Coli Exonuclease I, Exonuclease III, Exonuclease VII, T7 Exonuclease, BAL-31 Exonuclease, Lambda Exonuclease, RecJ$_f$, and Exonuclease T. Different nucleases have specificities for different types of nucleic acids making them useful for different applications. Exonuclease I catalyzes the removal of nucleotides from single-stranded DNA in the 3' to 5' direction. Exonuclease I degrades excess single-stranded primer oligonucleotide from a reaction mixture containing double-stranded extension products. Exonuclease III catalyzes the stepwise removal of mononucleotides from 3'-hydroxyl termini of duplex DNA. A limited number of nucleotides are removed during each binding event, resulting in coordinated progressive deletions within the population of DNA molecules. The preferred substrates are blunt or recessed 3'-termini, although the enzyme also acts at nicks in duplex DNA to produce single-strand gaps. The enzyme is not active on single-stranded DNA, and thus 3'-protruding termini are resistant to cleavage. The degree of resistance depends on the length of the extension, with extensions 4 bases or longer being essentially resistant to cleavage. This property can be exploited to produce unidirectional deletions from a linear molecule with one resistant (3'-overhang) and one susceptible (blunt or 5'-overhang) terminus. Exonuclease VII is a single-strand directed enzyme with 5' to 3'- and 3' to 5'-exonuclease activities making it the only bi-directional E. coli exonuclease with single-strand specificity. The enzyme has no apparent requirement for divalent cation, and is fully active in the presence of EDTA. Initial reaction products are acid-insoluble oligonucleotides which are further hydrolyzed into acid-soluble form. The products of limit digests are small oligomers (dimers to dodecamers). For additional information about nucleases see catalogues from manufacturers such as New England Biolabs, Beverly, Mass.

In some embodiments one of the primers added for PCR amplification is modified so that it is resistant to nuclease digestion, for example, by the inclusion of phosphorothioate. Prior to hybridization to an array one strand of the double stranded fragments may be digested by a 5' to 3' exonuclease such as T7 Gene 6 Exonuclease. In some embodiments the nucleic acid sample, which may be, for example, genomic DNA, is fragmented, using for example, a restriction enzyme, DNase I or a non-specific fragmentation method such as that disclosed in U.S. patent application Ser. No. 09/358,664, which is incorporated herein by reference in its entirety. Adaptors containing at least one priming site are ligated to the fragmented DNA. Locus-specific primers are synthesized which contain a different adaptor sequence at the 5' end. The adaptor-ligated genomic DNA is hybridized to the locus-specific primers and the locus specific primer is extended. This may be done for example, by the addition of DNA polymerase and dNTPs. Extension products may be amplified with primers that are specific for the adaptor sequences.

This allows amplification of a collection of many different sequences using a limited set of primers. For example, a single set of primers may be used for amplification. In another embodiment a second amplification step is carried out using the same or different primers.

In some embodiments the amplified products are analyzed by hybridization to an array of probes attached to a solid support. In some embodiments an array of probes is specifically designed to interrogate a collection of target sequences. The array of probes may interrogate, for example, from 1,000, 5,000, 10,000 or 100,000 to 2,000, 5,000, 10,000, 100,000, 1,000,000 or 3,000,000 different target sequences. In one embodiment the target sequences contain SNPs and the array of probes is designed to interrogate the allele or alleles present at one or more polymorphic location. The array may comprise a collection of probes that hybridize specifically to one or more SNP containing sequences. The array may comprise probes that correspond to different alleles of the SNP. One probe or probe set may hybridize specifically to a first allele of a SNP, but not hybridize significantly to other alleles of the SNP and a second probe set may be designed to hybridize to a second allele of a SNP but not hybridize significantly to other alleles. A hybridization pattern from the array indicates which of the alleles are present in the sample. An array may contain probe sets to interrogate, for example, from 1,000, 5,000, 10,000 or 100,000 to 2,000, 5,000, 10,000, 100,000, 1,000,000 or 3,000,000 different SNPs.

In another embodiment an array of probes that are complementary to tag sequences present in the capture probes is used to interrogate the target sequences. In some embodiments the amplified targets are analyzed on an array of tag sequences, for example, the Affymetrix GenFlex® array (Affymetrix, Inc., Santa Clara, Calif.). In this embodiment the capture probes comprise a tag sequence that is unique for each species of capture probe. A detectable label that is indicative of the allele present at the polymorphic site of interest is associated with the tag. The labeled tags are hybridized to the one or more arrays and the hybridization pattern is analyzed to determine which alleles are present.

In another embodiment methods for generating a plurality of different oligonucleotides are disclosed. Oligonucleotides may be synthesized in parallel on a solid support. Combinatorial chemistry may be used to generate degeneracy in the capture probe pool. The oligonucleotides are then released from the solid support and used for further analysis. The released probes may be used, for example, for multiplex PCR amplification of a collection of target sequences, for probes, for primers for reverse transcription or amplification or for any other use of oligonucleotides known in the art.

In one embodiment the oligonucleotides on the solid support comprise a collection of capture probes.

In another embodiment kits that are useful for the present methods are disclosed.

In one embodiment a kit for amplifying a collection of target sequences is disclosed. The kit may comprise one or more of the following: a collection of capture probes as disclosed, one or more adaptor, one or more generic primers for common sequences, one or more restriction enzymes, buffer, one or more polymerase, a ligase, buffer, dNTPs, ddNTPs, and one or more nucleases. The restriction enzyme of the kit may be a type-IIs enzyme. The capture probes may be attached to a solid support.

CONCLUSION

Methods are disclosed for genotyping a collection of polymorphisms using locus specific capture probes. The locus specific capture probes are synthesized as degenerate oligonucleotides, by for example, combinatorial chemistry. The use of degenerate probes allows for more cost effective probe synthesis. The polymorphisms may be selected based on proximity to a selected restriction site and proximity to a degenerate priming site. Capture probes may be synthesized on an array in a 3' to 5' direction and released from the array prior to being extended. Alternatively the probes may be synthesized in a 5' to 3' direction and extended on the array.

All publications and patent applications cited above are incorporated by reference in their entirety for all purposes to the same extent as if each individual publication or patent application were specifically and individually indicated to be so incorporated by reference. Although the present invention has been described in some detail by way of illustration and example for purposes of clarity and understanding, it will be apparent that certain changes and modifications may be practiced within the scope of the appended claims.

We claim:

1. A kit comprising at least 100 different species of capture probes for genotyping a plurality of polymorphic positions each present on a different target sequence:

wherein each target sequence comprises a common sequence that is within 1000 base pairs of the polymorphic position;

wherein each target sequence comprises a consensus sequence immediately adjacent to the common sequence wherein the consensus sequence comprises at least one base that is identical in all the target sequences and at least one base that is variable between target sequences;

wherein each capture probe comprises a first universal priming sequence and a target specific sequence that comprises a region that is complementary to the consensus sequence from one target sequence and a region that is complementary to the common sequence, wherein the capture probes are optionally pooled into 1 to 5 containers each containing a plurality of different species of capture probes; and wherein the kit further comprises an array of allele specific probes, the array comprising at least one allele specific probe for each allele of each polymorphic position in said plurality of polymorphic positions.

2. The kit of claim 1 wherein the array further comprises control probes that are identical to the allele specific probes except for the presence of a single base mismatch at the central position of each probe.

3. The kit of claim 1 wherein the common sequence is between 4 and 10 base pairs.

4. The kit of claim 1 wherein the common sequence is a recognition site for a restriction enzyme.

5. The kit of claim 1 wherein each polymorphism in the plurality is within 1000 base pairs of a recognition site for a selected restriction enzyme and wherein the polymorphic position is between said recognition site and said common and consensus sequences.

6. The kit of claim 5 wherein said selected restriction enzyme is Not 1.

7. The kit of claim 1 wherein said plurality of different species of capture probes are attached to a solid support selected from the group consisting of arrays, beads, microparticles, microtitre dishes and gels.

8. The kit of claim 7 wherein the capture probes are attached to the solid support through a covalent interaction and wherein optionally each species of capture probe is attached to the solid support in a discrete location.

9. The kit of claim 1 wherein the capture probes are synthesized in one or more pools by a series of separate and pooled monomer additions.

10. A kit comprising at least 100 different species of capture probes for genotyping a plurality of polymorphic positions each present on a different target sequence:
   wherein each target sequence comprises a common sequence that is within 1000 base pairs of the polymorphic position;
   wherein each target sequence comprises a consensus sequence immediately adjacent to the common sequence wherein the consensus sequence comprises at least one base that is identical in all the target sequences and at least one base that is variable between target sequences;
   wherein each capture probe comprises a first universal priming sequence and a target specific sequence that comprises a region that is complementary to the consensus sequence from one target sequence and a region that is complementary to the common sequence,
   wherein the capture probes are optionally pooled into 1 to 5 containers each containing a plurality of different species of capture probes;
   wherein each polymorphism in the plurality is within 1000 base pairs of a recognition site for a selected restriction enzyme and wherein the polymorphic position is between said recognition site and said common and consensus sequences; and
   further comprising an adaptor sequence comprising a single strand overhang that is complementary to the overhang generated by digestion with said selected restriction enzyme.

11. The kit of claim 10 further comprising a first primer for the adaptor and a second primer for the universal priming sequence and optionally comprising a polymerase, dNTPs, said selected restriction enzyme, and buffer.

12. A kit comprising at least 100 different species of capture probes for genotyping a plurality of polymorphic positions each present on a different target sequence:
   wherein each target sequence comprises a common sequence that is within 1000 base pairs of the polymorphic position;
   wherein each target sequence comprises a consensus sequence immediately adjacent to the common sequence wherein the consensus sequence comprises at least one base that is identical in all the target sequences and at least one base that is variable between target sequences;
   wherein each capture probe comprises a first universal priming sequence and a target specific sequence that comprises a region that is complementary to the consensus sequence from one target sequence and a region that is complementary to the common sequence,
   wherein the capture probes are optionally pooled into 1 to 5 containers each containing a plurality of different species of capture probes;
   wherein each polymorphism in the plurality is within 1000 base pairs of a recognition site for a selected restriction enzyme and wherein the polymorphic position is between said recognition site and said common and consensus sequences;
   wherein said plurality of different species of capture probes are attached to a solid support selected from the group consisting of arrays, beads, microparticles, microtitre dishes and gels; and
   wherein each capture probe further comprises a tag sequence that is unique for each species of capture probe and the capture probes are attached to the solid support by hybridization to a collection of tag probes that are covalently attached to the solid support.

* * * * *